United States Patent [19]

Lundback

[11] Patent Number: 4,736,749
[45] Date of Patent: * Apr. 12, 1988

[54] HOLDER FOR MEDICAL USE FIXED BY VACUUM

[75] Inventor: Stig Lundback, Vaxholm, Sweden

[73] Assignee: Astra-Tech Aktiebolag, Stockholm, Sweden

[*] Notice: The portion of the term of this patent subsequent to Mar. 3, 2004 has been disclaimed.

[21] Appl. No.: 849,482

[22] Filed: Apr. 4, 1986

[30] Foreign Application Priority Data

Apr. 26, 1985 [SE] Sweden .............................. 8502048

[51] Int. Cl.$^4$ .............................................. A61B 5/04
[52] U.S. Cl. ..................................... 128/643; 128/802
[58] Field of Search ................. 128/643, 639–640, 128/641, 802–803

[56] References Cited

U.S. PATENT DOCUMENTS

| | | | |
|---|---|---|---|
| 2,660,175 | 11/1953 | Thrasher et al. | 128/643 |
| 3,490,442 | 1/1970 | Streu | 128/643 |
| 3,505,993 | 4/1970 | Lewes et al. | 128/643 |
| 3,640,270 | 2/1972 | Hoffman | 128/643 |
| 4,369,793 | 1/1983 | Staver | 128/643 |
| 4,556,065 | 12/1985 | Hoffman | 128/643 X |

FOREIGN PATENT DOCUMENTS

| | | | |
|---|---|---|---|
| 1108820 | 6/1961 | Fed. Rep. of Germany | 128/643 |
| 0639524 | 2/1979 | U.S.S.R. | 128/643 |

*Primary Examiner*—William E. Kamm
*Assistant Examiner*—Angela D. Sykes
*Attorney, Agent, or Firm*—Brumbaugh, Graves, Donohue & Raymond

[57] ABSTRACT

The invention relates to a holder for diagnostic and therapeutic devices fixed by vacuum. Vacuum is supplied by a hose or tube (8), in which one or several electrical conductors (7) for electrical power supply or signal transmission are drawn. The holder comprises a rigid backpiece (3), an intermediate elastomeric element (2), and the diagnostic or therapeutic device (1). The intermediate element (2) comprises a comparatively stiff sealing ring (9), which in a working state is supported against the skin by a sealing lip (13) and with its opposite side against the backpiece (3). The device (1) is rigidly connected to the backpiece (3), but the sealing ring of the intermediate element (2) is movable and, outwardly from the backpiece, slightly resilient (via resilient means 17). When the lip-side of the ring is not loaded and the ring thus pressed outwardly, a vacuum valve is closed automatically through the action of the intermediate component, and is re-opened when the holder is pressed against the surface of the skin, whereupon the holder is held firmly by suction.

8 Claims, 1 Drawing Sheet

U.S. Patent
Apr. 12, 1988
4,736,749
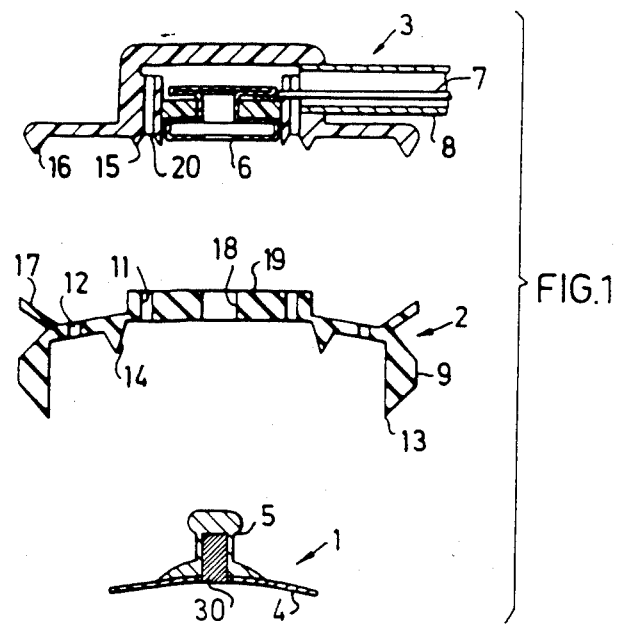
FIG.1
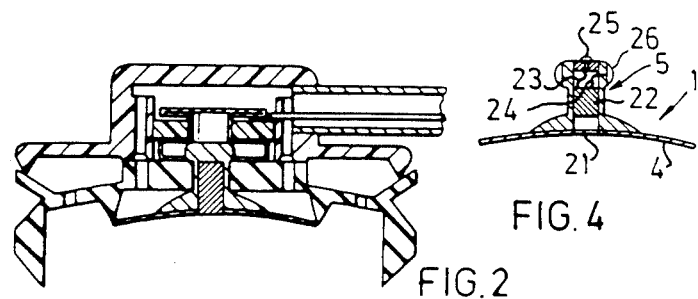
FIG.2
FIG.4
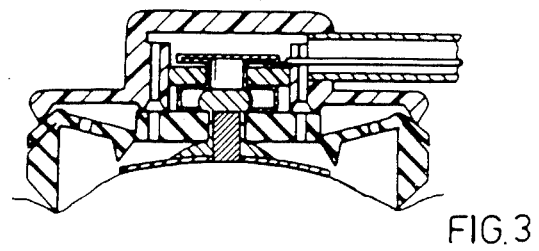
FIG.3

HOLDER FOR MEDICAL USE FIXED BY VACUUM

BACKGROUND OF THE INVENTION

The invention relates to a holder for the attachment of diagnostic and therapeutic devices to the skin at a certain predetermined site of the human body.

Diagnostic and therapeutic devices intended to be attached to the human body for a longer period than a few seconds are normally kept in place by adhesive tape, by fixation with rubber bands or in a similar way. For ECG-electrodes, fixation arrangements of an essentially different kind have been described where fixation is achieved with the aid of vacuum.

Said known arrangements for fixation display various drawbacks. The method of attachment by adhesive tape is simple but does not provide for the easy displacement of the device to another site of the skin, in case it had not been put in the right place from the beginning. Moreover, adhesive tape may cause inconvenience when removed from areas with hair growth, may fall off through the effect of transpiration, or may, in the case of uncautious handling during application, fasten in places not considered for application. With said fixation arrangements, it is moreover not easy to bring into skin contact diagnostic and therapeutic devices in a way that guarantees a constant force over time to be exerted by the device onto the skin. Keeping the force of attachment constant is important in, e.g., receiving electrical or acoustic signals through the skin.

An ECG-electrode integrated arrangement for attachment displaying the characteristics of the preamble of claim 1, which is thus considered to be fastened by vacuum provided through a tube, and which has a valve in closed position when the electrode is not being attached opening automatically when it is applied, and closing automatically when the electrode falls off, is known by the Austrian patent specification No. 248608.

According to an embodiment described there, a spring-biassed electrode plate with the aid of an elastic diaphragm is coupled to a surrounding sealing ring. When the electrode plate is pressed against the skin of a patient, a valve opens and vacuum is applied to a cavity extending around the electrode, delimited by the sealing ring.

Unfortunately, it has been found that the electrode plate abuting against the skin becomes swiveling and axially movable in relation to the sealing ring, resulting in inferior skin attachment and in a varying contact between the skin and the electrode when there is movement.

A holder integrated with an ECG-electrode, which is held in position by means of vacuum and which has a surrounding sealing ring which is relatively rigidly connected to a centrally located electrode plate, is known from the U.S. Pat. No. 4,248,243. With this electrode, however, suction cannot be applied through a tube from a central vacuum source, since it lacks the self-closing valve of the Austrian patent, which valve cannot be combined with the rigid design. In addition to that, the arrangement described in the US patent specification is highly disturbing since it emits a whizzing noise arising in the ejector suction element.

SUMMARY OF THE INVENTION

An object of the invention is to provide a holder for attaching various diagnostic or therapeutic devices to the skin that is easy to attach, remains firmly in place, is easy to detach from the skin and can be readily moved from one site to another. In particular, a holder, according to the invention, comprises a rigid backpiece, to which the diagnostic or therapeutic arrangement is attached, and a seal element joined to the backpiece and surrounding the diagnostic or therapeutic arrangement. The seal element comprises a sealing ring at the perimeter that ends in a sealing lip that is engageable with the skin. In a working state of the holder, the vacuum is communicated to a region under the seal element within the sealing lip. A deformable portion of the seal element allows movement of the sealing ring, which movement opens a valve in the form of a rib on the seal element that engages the therapeutic arrangement, thereby allowing the vacuum connection to the seal element that holds the holder securely against the skin. In an inactive state, a resilient force applied to the seal element urges it away from the backpiece such that the aforementioned valve closes. The opening of the valve occurs automatically when the holder is pressed against the skin, thereby moving the seal element against the resilient force.

Diagnostic devices intended to be attached to the skin by means of the present vacuum-fixed holder are, for example, electrodes for electroencephalography (ECG), electrodes for electromyography (EMG), sensors for skin temperature, humidity, and pH, biosensors and other sensors for indirect or direct measurement of blood gases, intramuscular sensor probes for, e.g., measurement of local peripheral circulation by laser-Doppler techniques, microphones for the registration of heart sounds, optical conductors for observation of the skin, etc.

Therapeutic devices intended to be attached to the skin by means of the present vacuum-fixed holder are, e.g., electrodes for electrical stimulation of muscles, defibrillators, injectors for intramuscular administration of pharmaceuticals, electrodes for hyperthermal treatment, devices for percutaneous administration of pharmaceuticals, etc.

In accordance with an advantageous aspect, the invention may be realized in embodiments of partially disposable sort or with easily exchangeable parts which are sterilizable.

The diagnostic or therapeutic arrangement may be rigidly or removably connected to the vacuum-fixed holder. If removably connected, the connection may advantageously be made according to the press-stud connection principle, commonly called a "snap fastener".

DESCRIPTION OF THE DRAWINGS

The invention will now be described with reference to an exemplifying but not limiting embodiment thereof. In this context, FIG. 1 shows an exploded sectional view of a holder consisting of three components.

FIG. 2 shows a sectional view of a holder in idle position and

FIG. 3 shows a sectional view of a holder in active position that is, with the holder attached to the skin.

FIG. 4 is a sectional view of an exemplary diagnostic arrangement.

DESCRIPTION OF PREFERRED EMBODIMENT

The various parts of the embodiment are best seen from FIG. 1. The diagnostic or therapeutic arrangement has a preferentially flat surface or a surface which is slightly concave with respect to the skin. Its outer form is determined by the cooperation with the other components of the holder described here. The diagnostically or therapeutically operative part 30 of the arrangement 1 is preferentially arranged at or near surface 4. The operative part 30 is connected to a recorder or to an electrical power source not shown in FIGS. 1-3. Arrangement 1 on the side opposite to surface 4 is provided with a stem 5, forming the male part of a press-stud connector that can be fastened in the female part 6 of the connector in a backpiece 3, which female part thereby penetrates a hole 18 in an intermediate element 2, which, i.a., comprises sealing ring 9. It is a resilient press-stud connector of a type in common use. Although not shown in FIGS. 1-3, the male and female parts of the press-stud connector comprise a number of isolated electrical and other contacts necessary for the transmission of signals or power. The backpiece 3 may be advantageously made of non-conducting plastics, eventually provided with some sort of electrical shielding not shown here. To backpiece 3, there is connected a vacuum hose or tube communicating with a vacuum pump or a reservoir, in which the shielded electrical conductors are drawn to the female part 6. When the press-stud connection is made via 5,6, the diagnostic or therapeutic arrangement 1 is thus rigidly connected to the backpiece and, via the lead or bundle of conductors 7, communicates with measuring equipment or a power source of known type. The vacuum tube 8 is connected to a cavity in backpiece 3 and, circumferentially to the press-stud connector part 6, there are provided a number of holes 20.

When the three parts in FIG. 1 are assembled, the configuration shown in FIG. 2 is obtained. For the sake of clarity, only FIG. 1 has been provided with reference numbers, but a comparison is easy to make anyway. In the example shown, parts 1 and 2 are rotationally symmetric which simplifies manufacture but is not absolutely necessary.

Part 2, which is made from silicone rubber or a similar material, has a relatively rigid ring portion 9 with a circumferential sealing lip 13, which in use is sealing against the skin. To start with, the function in an idle state will be described.

It is obvious that the relatively flat central portion of intermediate element 2 provided with hole 18 will abut against the sealing lip 15 in backpiece 3. The front side of the central portion via circumferentially arranged holes 11 communicates with the rear side of intermediate element 2, on which there is arranged another sealing lip 14. This lip will abut against the rear side of the diagnostic or therapeutic arrangement 1, and both lip 14 and 15 will seal off a volume around the central portion of part 1 being put under vacuum, whereby a certain bending of the central portion of intermediate element 2 occurs to which also contributes that flange 17 on the intermediate part 2 is elastically abuting against lip 16 on backpiece 3. With the configuration in FIG. 2, notwithstanding unsignificant leakage, only said volume around the central part of arrangement 1 will be put under vacuum.

When the electrode, being in a configuration according to FIG. 2, is attached to a skin surface, the following will occur. When the circumferential lip is pressed against the skin, the force will affect flange 17 via the relatively rigid ring 9, which is resiliently deformed, whereby the central part of intermediate element 2 is more excessively deformed and lip 14 eases away from the rear side of arrangement 1. The space between the skin and the intermediate element 2 is placed in communication with the vacuum source, and since the intermediate element 2 is provided with holes 12 in its peripheral part, all spaces will be placed under vacuum, the sealing lips 13 and 16 therewith sealing between the backpiece 3 and the skin. The configuration illustrated in FIG. 3 is thereby obtained.

It will be clear from FIG. 3 that the backpiece 3 and the ring 9 now function as an interlocking composite assembly. Although the ring 9 is urged outwardly, away from the backpiece 3 by an elastic deformation force acting through the flange 17, this force is quite insignificant in comparison with the pneumatic forces. The vacuum used need not reach more than 0.1 kg/cm$^2$. The air pressure then exerts against the skin a force which corresponds substantially to the force exerted by the surface embraced by lip 13. This force is counter-acted by the resistance normally offered by the skin, the greater part of which resistance is exerted on the undersurface 4 of arrangement 1, thereby to achieve particularly good contact. Due to the deformation of the skin, there is also obtained a certain shape-conforming effect which prevents slipping. A break force applied via hose 8 will cause the skin to accompany the movement until deformation is too great and the lip 13 is no longer able to provide a seal, whereupon the electrode will fall off, and the resilient flange returns to the position shown in FIG. 2, with the valve seal once again in effect.

Thus, in order to obtain good functioning, the surface 4 of arrangement 1 in the position shown in FIG. 3 must be inwardly drawn relative to the lip 13 on the ring 9. With a diameter of 30 mm for the lip, the surface is suitably inwardly drawn to a depth of 3-4 mm.

The described embodiment has been shown to function extremely well. For example, arrangement 1 comprising a micro electret microphone has made possible the objective recording of heart sounds. Recording of heart sounds with simultaneous recording of ECG provides valuable information in various types of heart defects. The position of the microphone may be easily changed until the optimal position for the registration of the respective heart sound has been found. A microphone amplifier can be integrated in arrangement 1 in order to further improve signal quality.

An arrangement of known type as such for the registration of acoustic signals is shown in FIG. 4. The sound is transferred from the skin to the diaphragm 21 and, from there, to the microphone 22. Conductors 23 and 24 connect the microphone with contacts 25 and 26 at the male part 5 of the press-stud connector. The female connector part not shown here has been arranged to fit contacts 25 and 26 and has two conductors isolated from each other, which together constitute conductor bundle 7 in the vacuum tube 8 and lead to the recording instrument not shown here.

Arrangement 1 can be easily adapted to comprise other diagnostic and therapeutic arrangements mentioned before.

The good fixation of the holder provides for the recording of heart sounds, temperature, measurement of blood gases, etc., even in the case of physical activity, for example in examinations under physical exercise.

The presence of dense body hair does not prevent the holder from remaining firmly seated. Because of the negative pressure being small, the holer may remain attached for a long period of time without suction marks appearing on the skin, except for a slight red ring where lip 13 abuts the skin.

The press-stud connection between the diagnostic or therapeutic element 1 and the backpiece 3 makes the former easily exchangeable. This makes possible that new or sterilized used parts can be rapidly placed on the holder, which may be used for the next patient. The elastomer element 2 can be made of sterilizable material and be used repeatedly. The invention thereby is exceptionally practical and hygienic. When it is used under conditions with increased transpiration, it may be appropriate to mount in the holder some moisture-absorbing material, e.g. a disk of fibrous material, which can be inserted between the elastomer element and the backpiece, and which may be discarded after use.

I claim:

1. A holder for diagnostic or therapeutic devices, for attachment to the skin by the action of vacuum provided through a hose from a vacuum source, and which comprises a diagnostic or therapeutic arrangement (1), which is adapted to be connected to a measuring instrument or an electrical power source (via 7) or both, and which holder is adapted to be attached with a front side (4) engaging a skin surface, and which comprises a rigid backpiece (3), to which is attached the diagnostic or therapeutic arrangement (1) and a sealing means (2), which surrounds said arrangement (1) and comprises a sealing ring (9), circumferentially arranged around said arrangement (1) and ending in a sealing lip (13), which sealing ring (9) in a working state is adapted to abut against said skin surface such that a volume connected to the vacuum source is delimited by said skin surface and the sealing means, characterized in that said arrangement (1) and the sealing lip (13) are movably arranged with respect to each other under action of a resilient force (via 17), which urges said arrangement (1) and a plane defined by said sealing lip (13) away from each other, from a working state (FIG. 3) to an idle state (FIG. 2), which movement activates valve means for closing the supply vacuum to said volume under vacuum, in that said arrangement (1), in both a working state and an idle state, remains stationary relative to the backpiece (3), and in that the sealing lip (13) is situated on a movable ring (9), which is supported against the backpiece (3) in said working state.

2. A holder according to claim 1, characterized in that both the diagnostic or therapeutic arrangement (1) and the sealing means (2) are components separate from each other and from the backpiece (3) and are detachably connected to each other and to the backpiece (3), whereby they may be removed from the backpiece and replaced by like components.

3. A holder according to claim 2, characterized in that the sealing means (2) comprises an elastomeric element (2) in a single piece, which includes said sealing ring (9) incorporating the sealing lip (13), in that the sealing ring on the part thereof remote from the sealing lip includes a diaphragm disk with a central hole (18), through which a stem part of the arrangement (1) is adapted to pass, and in that the backpiece (3) is provided with holding means (6) for that stem part (5).

4. A holder according to claim 3, characterized in that the means for detachably holding the arrangement (1) to the backpiece includes a snap fastener device.

5. A holder according to claim 3, and further characterized in that the elastomeric element includes resilient means (17) compressible in the working state into resilient engagement with the backpiece and thereupon biasing the element away from the backpiece, in that a first seal-forming means (15) forms a seal between the elastomeric element and the backpiece, in that at least one opening (11) through the elastomeric element within the seal of the first seal-forming means is adapted to communicate a vacuum from the source through the elastomeric element and in that said valve means includes second seal-forming means (14) forming a seal between the elastomeric element and the diagnostic or therapeutic arrangement (1) when the resilient means (17) is in an uncompressed state, whereby communication between a vacuum from the vacuum source and the atmosphere external of the elastomeric element and the arrangement is prevented in the idle state, said seal formed by the second seal-forming means being broken when the sealing ring (9) is moved toward the backpiece againsnt the bias of the resilient means (17) in the working state, whereby vacuum is communicated to said volume.

6. A holder according to claim 5, and further characterized in that the resilient means (17) is a flange (17) extending circumferentially of and outwardly from the elastomeric element, the flange (17) being adapted to form a seal with a sealing lip portion (16) on the backpiece (3) in the working state, the flange being outwardly of the second seal-forming means (14), relative to the opening (11), and wherein the elastomeric element has at least one aperture (12) for communication of a vacuum in the working state to a region of the backpiece bounded by the first and second seal-forming means (15), whereby in the working state a force due to the applied vacuum urges the backpiece (3) toward said surface against the bias of the resilient means (17), which force retains the holder attached to said surface with the arrangement in engagement therewith.

7. A holder according to claim 1 and further characterized in that the arrangement (1) has a frontal surface (4) adapted to engage the skin surface in the working position and in that said front surface is spaced-apart from the plane of the sealing lip (13) in a direction toward the backpiece (3) when the holder is in the working position.

8. A holder according to claim 7, characterized in that the frontal surface (4) of the arrangement (1) is concave.

* * * * *